(12) United States Patent
Siegrist et al.

(10) Patent No.: US 8,303,911 B2
(45) Date of Patent: Nov. 6, 2012

(54) CENTRIFUGAL MICROFLUIDIC SYSTEM FOR NUCLEIC ACID SAMPLE PREPARATION, AMPLIFICATION, AND DETECTION

(75) Inventors: Jonathan P. Siegrist, Walnut Creek, CA (US); Robert A. Gorkin, III, Exton, PA (US); Regis Peytavi, Irvine, CA (US); Marc Madou, Irvine, CA (US); Horacio Kido, Niland, CA (US); Mary Amasia, Irvine, CA (US); Emmanuel Roy, Montreal (CA); Teodor Veres, Montreal (CA)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/904,794

(22) Filed: Oct. 14, 2010

(65) Prior Publication Data

US 2011/0111987 A1    May 12, 2011

Related U.S. Application Data

(60) Provisional application No. 61/252,917, filed on Oct. 19, 2009.

(51) Int. Cl.
*C12M 1/33* (2006.01)
*C40B 60/12* (2006.01)
(52) U.S. Cl. ............... 422/506; 435/91.2; 435/173.1; 435/306.1; 506/39
(58) Field of Classification Search .......... 422/503, 422/506; 435/288.4, 306.1, 91.2, 173.1; 506/39
See application file for complete search history.

(56) References Cited

U.S. PATENT DOCUMENTS

| 5,882,903 | A * | 3/1999 | Andrevski et al. | 435/91.2 |
|---|---|---|---|---|
| 8,101,138 | B2 * | 1/2012 | Lee et al. | 422/506 |
| 2002/0115201 | A1 * | 8/2002 | Barenburg et al. | 435/306.1 |
| 2006/0165725 | A1 * | 7/2006 | Bozdayi | 424/227.1 |

(Continued)

FOREIGN PATENT DOCUMENTS
WO    WO 2009/009900 A1    1/2009

OTHER PUBLICATIONS

Alexandre, I. et al., Product Application Focus: Compact Disc with Both Numeric and Genomic Information as DNA Microarray Platform, BioTechniques 33:435-439 (Aug. 2002).

(Continued)

*Primary Examiner* — In Suk Bullock
*Assistant Examiner* — Timothy G Kingan
(74) *Attorney, Agent, or Firm* — Vista IP Law Group LLP

(57) ABSTRACT

A microfluidic system for processing a sample includes a microfluidic CD in the form a rotatable disc, the disc containing a plurality of separate lysis chambers therein. A magnetic lysis blade and lysis beads are disposed in each of the lysis chambers and a plurality of stationary magnets are disposed adjacent to and separate from the microfluidic CD. The stationary magnets are configured to magnetically interact with each of the magnetic lysis blades upon rotation of the microfluidic CD. Each lysis chamber may have its own separate sample inlet port or, alternatively, the lysis chambers may be connected to one another with a single inlet port coupled to one of the lysis chambers. Downstream processing may include nucleic acid amplification using thermoelectric heating as well as detection using a nucleic acid microarray.

13 Claims, 8 Drawing Sheets

U.S. PATENT DOCUMENTS

| | | |
|---|---|---|
| 2007/0125942 A1 | 6/2007 | Kido |
| 2008/0110500 A1 | 5/2008 | Kido et al. |
| 2008/0199930 A1* | 8/2008 | Lee et al. .................. 435/173.1 |
| 2008/0200343 A1* | 8/2008 | Clemens et al. .................. 506/9 |
| 2008/0300148 A1* | 12/2008 | Lee et al. ........................ 506/39 |
| 2009/0035847 A1* | 2/2009 | Cho et al. .................. 435/289.1 |
| 2009/0221431 A1* | 9/2009 | Yoo .................................. 506/9 |
| 2010/0075863 A1* | 3/2010 | Lesho et al. ...................... 506/9 |

OTHER PUBLICATIONS

Cho, Y. et al., One-step pathogen specific DNA extraction from whole blood on a centrifugal microfluidic device, Lab Chip, 7:565-573 (2007).

Ducree, J. et al., The centrifugal microfluidic Bio-Disk platform, J. Micromech, Microeng, 17:S103-S115 (2007).

Kido, H. et al., A novel, compact disk-like centrifugal microfluidics system for cell lysis and sample homogenization, Colloids and Surfaces B:Biointerfaces 58:44-51 (2007).

Kim, J. et al., Cell lysis on a microfluidic CD (compact disc), Lab Chip, 4:516-522 (2004).

Madou, M. et al., Lab on a CD, Annu. Rev. Biomed Eng., 8:601-628 (2006). Downloaded from arjournalsannualreviews.org by University of California—Irvine on Oct. 17, 2006.

Martensson, G. et al., Rapid PCR amplification of DNA utilizing Coriolis effects, Eur Biophys J., 35:453-458 (2006).

Centrifugal microfluidic platforms for rapid IVDs, published on IVD Technology (http://www.ivdtechnology.com) Oct. 7, 2010 (9 pages).

* cited by examiner

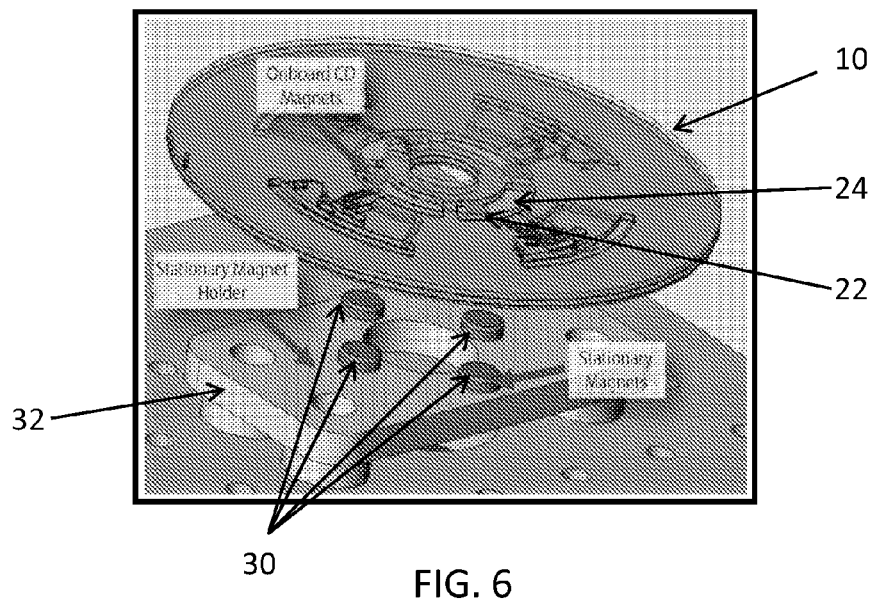
FIG. 6
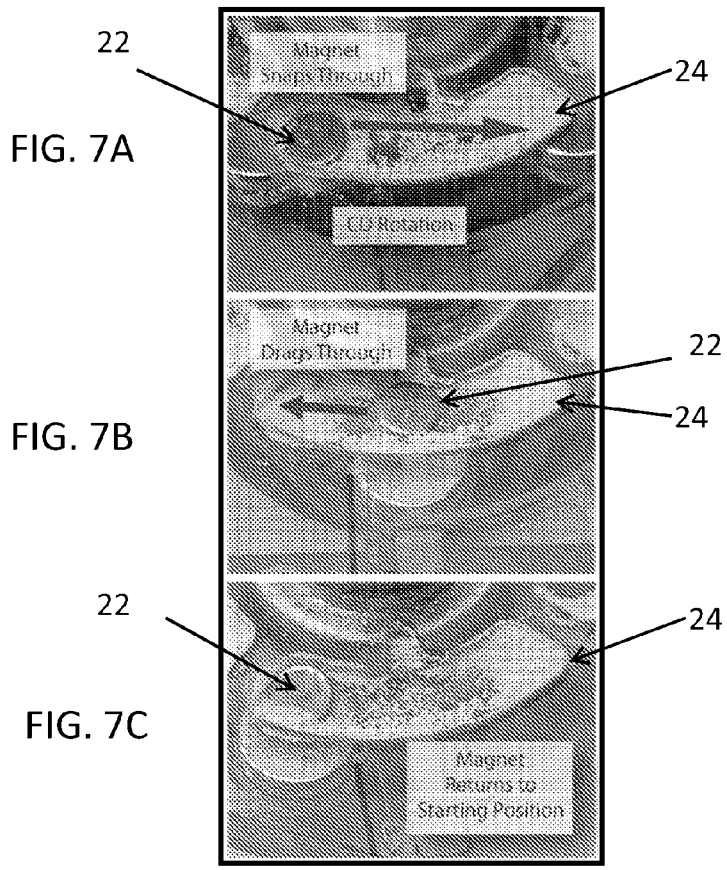
FIG. 7A
FIG. 7B
FIG. 7C

CENTRIFUGAL MICROFLUIDIC SYSTEM FOR NUCLEIC ACID SAMPLE PREPARATION, AMPLIFICATION, AND DETECTION

RELATED APPLICATION

This Application claims priority to U.S. Provisional Patent Application No. 61/252,917 filed on Oct. 19, 2009. U.S. Patent Application No. 61/252,917 is incorporated by reference as if set forth fully herein. Priority is claimed pursuant to 35 U.S.C. §119 and any other applicable statute.

FIELD OF THE INVENTION

The field of the invention generally relates to microfluidic devices and platforms for biological analysis. In particular, the invention pertains to centrifugal, compact disc (CD) devices that are utilized in a single system or platform to perform multiple processes. In particular, the device and method relate to a single platform that enables the rapid and automated processing of nucleic acid samples for both research and clinical settings. Exemplary processes include viral/cell lysis, sample clarification, and nucleic acid amplification (e.g., polymerase chain reaction (PCR)), and nucleic acid detection (e.g., real-time PCR or DNA microarray).

BACKGROUND OF THE INVENTION

Nucleic acid analysis is used in a variety of clinical and research applications. Traditionally, a separate nucleic acid (NA) analysis step was performed by hand in a bench top setting, which requires relatively large amounts of material, labor, and time. For example, in order to undergo nucleic acid analysis, a sample must first be prepped for analysis. Whole blood samples must first be processed to separate red blood cells from the sample. In other samples, for instance, a respiratory sample there may be fewer or no processing steps. Nonetheless, the sample must be lysed, purified, amplified, and then detected, all in separate, manual steps. These steps are labor-intensive and also traditionally require varied and expensive laboratory equipment. There is a need to scale down nucleic acid analysis and detection into an automated device that is capable of performing all the various steps in NA analysis.

Previous CD platforms have accomplished lysing by combining cell samples with grinding media (milling beads) and exposing the system to intense mixing by rapid and abrupt motion of the container. Lysis initially occurred due to collisions between milling beads and cells, causing puncture by direct collision and friction based shearing. However, in this system a secondary lysis mechanism took place when alternating the spin directions, causing impaction and friction due to Coriolis effects in the CD chamber. Another CD system improved on this by replacing the Coriolis-induced lysis with stronger magnetic-assisted bead beating. For example, U.S. Patent Application Publication No. 2007-0125942 discloses examples of this. Generally, strong magnets placed loosely in the CD were actuated by permanent magnets in a stationary platform causing additional impaction and lysis in the radial direction. The main limitation of the stand-alone systems remained the possibility for integration with other processing steps.

This invention combines elements of both Coriolis induced lysis and magnetically assisted lysis to create a superior CD-based lysis system that is integrated with additional processing steps.

SUMMARY

In one aspect of the invention, a system for sample lysis and homogenization on a centrifugal (CD) microfluidic platform has been developed. This performs a step essential to any nucleic acid analysis process. The system includes a stationary stand with permanent magnets placed beneath the CD and the CD itself, which contains ferromagnetic blades and lysis beads. As the CD spins over the stationary magnets, each lysis chamber is subjected to a radial, oscillating magnetic field and in turn, the magnetic blades are oscillated inside of the CD's lysis chambers. The movement of the blades creates a snap-and-drag motion, resulting in forces between the chamber walls and the lysis beads that create mechanical impaction and shear. The resulting forces disrupt cells/viruses and homogenize the sample via mechanical bead-beating.

The lysis CD platform can perform bead-beating lysis and homogenization on multiple, separate samples (e.g., four samples, each 50-75 µL in volume) or a single 200-300 µL sample that is then metered among the multiple (e.g., four) chambers. This is followed by a centrifugal-based clarification step that separates solid particulates/debris and leaves nucleic acid suspended in the supernatant. After a volume definition step, a unique siphon is used to transfer the now-clarified sample containing nucleic acid for removal. The delivered sample is ready for direct nucleic acid amplification and/or detection. The system has been tested and verified using both cells (bacterial spores) and viruses (influenza).

In addition to its utility, the system features additional centrifugal, microfluidic features including sample pre-metering, hydraulic-capillary valving, prevention of siphon re-priming, and self-venting.

Several additional microfluidic features may also be implemented. First, sample pre-metering can be implemented. This allows the insertion of a single sample into the CD, and splitting up of the sample equally between multiple, separate chambers (e.g., four chambers). Of course, there could be more or less chambers. Second, a hydraulic capillary valve is implemented. This is a surface-tension based capillary valve used on a CD, but is not exposed to atmospheric pressure behind the valve. This means that, in addition to the normal capillary forces present on the capillary valve, there is a low-pressure environment behind that liquid. This double-force, hydraulic capillary valve allows higher rotation speeds to be achieved as compared to a normal, single-force capillary valve. This translates to the ability to perform more efficient lysis at higher speeds without worry of the sample bursting into the next chamber prematurely.

Third, siphons on centrifugal microfluidic platforms often re-prime after their initial use, due to liquid remaining behind the siphon. Re-priming, unfortunately, can clog the system fluidics, and prevent liquids from moving further downstream. This problem has been solved by placing a capillary valve in-line with the siphon. This prevents liquid from re-priming the siphon at low speeds and disrupting further fluidic functions. Fourth, self-venting has been implemented. Before operation, the sample inlet port(s) and the sample removal ports are all sealed using a seal such as an adhesive film. This means the entire system is closed, with no exposure to the outside environment. The practicality-of-use implications are that the CD can be used in any standard molecular biology lab or clinic without concerns of contaminating the area with direct liquid samples or aerosols. The self-venting channel allows air to continue through the system and replace liquid behind it as it is processed, keeping the entire system in equilibrium and ensuring that no negative or positive pressures develop while the system is closed.

Advantages of the invention include that feature that much less is time needed for a total analysis (<10 minutes) on the centrifugal platform, as compared to ~30 minutes for performing the same steps by hand on standard bench-top equipment. Another advantage is that less human error is involved, as each step is handled by the platform. There also is less labor required—the system is automated, except for the initial sample introduction. Further, by operating in the microfluidic regime, this allows use of smaller reagent volumes which leads to less cost. The system also has higher throughput, meaning that the system can be used to process multiple samples at once.

In another aspect of the invention, additional nucleic acid analysis functions can occur after sample preparation, in an integrated fashion, on the CD. Such additional processing steps include amplification and detection. This allows for a complete, integrated, and automated nucleic acid analysis from sample to answer.

In still another aspect of the invention, nucleic acid analysis using a microarray (e.g., DNA microarray) may be integrated with the microfluidic CD. The microarray may be a modular component that is inserted or loaded into the microfluidic CD. Alternatively, the microarray may be integrated on-board the microfluidic CD.

In another aspect of the invention, a system for processing a sample includes a microfluidic CD in the form a rotatable disc, the disc containing a plurality of separate lysis chambers therein, each lysis chamber having a separate inlet port configured to load samples into each respective lysis chamber. A magnetic lysis blade and lysis beads are disposed in each lysis chamber. A plurality of clarification chambers are disposed radially outward of the lysis chambers, each clarification chamber connected to an associated lysis chamber via a hydraulic capillary valve. The system includes a plurality of stationary magnets disposed adjacent to and separate from the microfluidic CD, the plurality of stationary magnets configured to magnetically interact with each of the magnetic lysis blades upon rotation of the microfluidic CD. Each inlet port is configured to be sealed from the external environment.

In another embodiment, a system for processing a sample includes a microfluidic CD in the form a rotatable disc, the disc containing a plurality of separate lysis chambers therein, each lysis chamber being connected to an adjacent lysis chamber via a connection channel, one of the lysis chambers further comprising an inlet port configured to load a sample into the lysis chambers. A magnetic lysis blade and lysis beads are disposed in each of the lysis chambers. A plurality of clarification chambers are disposed radially outward of the lysis chambers, each clarification chamber connected to an associated lysis chamber via a hydraulic capillary valve. The capillary valve(s) may be modified or optimized as needed to act as a filter in order to reduce or eliminate the risk of downstream clogging. A plurality of stationary magnets are disposed adjacent to and separate from the microfluidic CD, the plurality of stationary magnets configured to magnetically interact with each of the magnetic lysis blades upon rotation of the microfluidic CD. The connection channel is dimensioned to prohibit transfer of the magnetic lysis blade and lysis beads but does allow for the passage of fluids.

In another embodiment, a system for processing a sample includes a microfluidic CD in the form a rotatable disc, the disc containing a plurality of separate lysis chambers therein, each lysis chamber having a separate inlet port configured to load samples into each respective lysis chamber. A magnetic lysis blade and lysis beads are disposed in each lysis chamber. A plurality of stationary magnets are disposed adjacent to and separate from the microfluidic CD, the plurality of stationary magnets configured to magnetically interact with each of the magnetic lysis blades upon rotation of the microfluidic CD. The system includes a thermoelectric device configured to heat or cool the microfluidic CD, the thermoelectric device being moveable relative to the microfluidic CD. A plurality of PCR chambers are disposed in the microfluidic CD and radially outward of the lysis chambers, each PCR chamber operatively coupled to one of the lysis chambers, the PCR chamber containing therein PCR reagents. A plurality of exonuclease chambers are disposed in the microfluidic CD, each exonuclease chamber configured to receive nucleic acid from a respective PCR chamber, the exonuclease chambers containing therein exonuclease. At least one nucleic acid microarray is configured to receive nucleic acid from at least one of the plurality of exonuclease chambers.

BRIEF DESCRIPTION OF THE DRAWINGS

FIG. 6 is a schematic illustration showing the microfluidic CD system along with the underlying stationary permanent magnets.

FIGS. 7A-7C illustrate a sequence of photographic images illustrating the snap-drag motion of the magnetically responsive elements as the magnetic lysis "blades" interact with the stationary off-CD magnets upon rotation of the CD body.

FIG. 10A illustrates four (4) circularly-arrayed devices dedicated to four (4) multiplexed detection assays.

FIG. 11A illustrates lysis in the clockwise direction, while FIG. 11B illustrates lysis in the counterclockwise direction (note that the capillary valves at the lysis chamber exit and hybridization buffer reservoir are still holding). FIG. 11C illustrates clarification, also causing bursting and filling of the first serial siphon capillary valve of the hybridization buffer reservoir. In FIG. 11D the lysis chamber finishes emptying and the PCR volume is defined. In FIG. 11E the PCR microchamber fills uniformly, and the 1st serial siphon on the hybridization buffer reservoir primes. In FIG. 11F, the exonuclease (PCR) chamber fills and the 2nd serial siphon capillary valve bursts. In FIG. 11G the exonuclease siphon primes, and the final serial siphon on the hybridization buffer reservoir primes. In FIG. 11H the mixing chamber fills with two liquids. FIG. 11I illustrates mixing occurring. FIG. 11J illustrates the mixing chamber emptying into what would be the DNA hybridization layer of the CD (not shown).

DETAILED DESCRIPTION OF THE INVENTION

Figure 1:
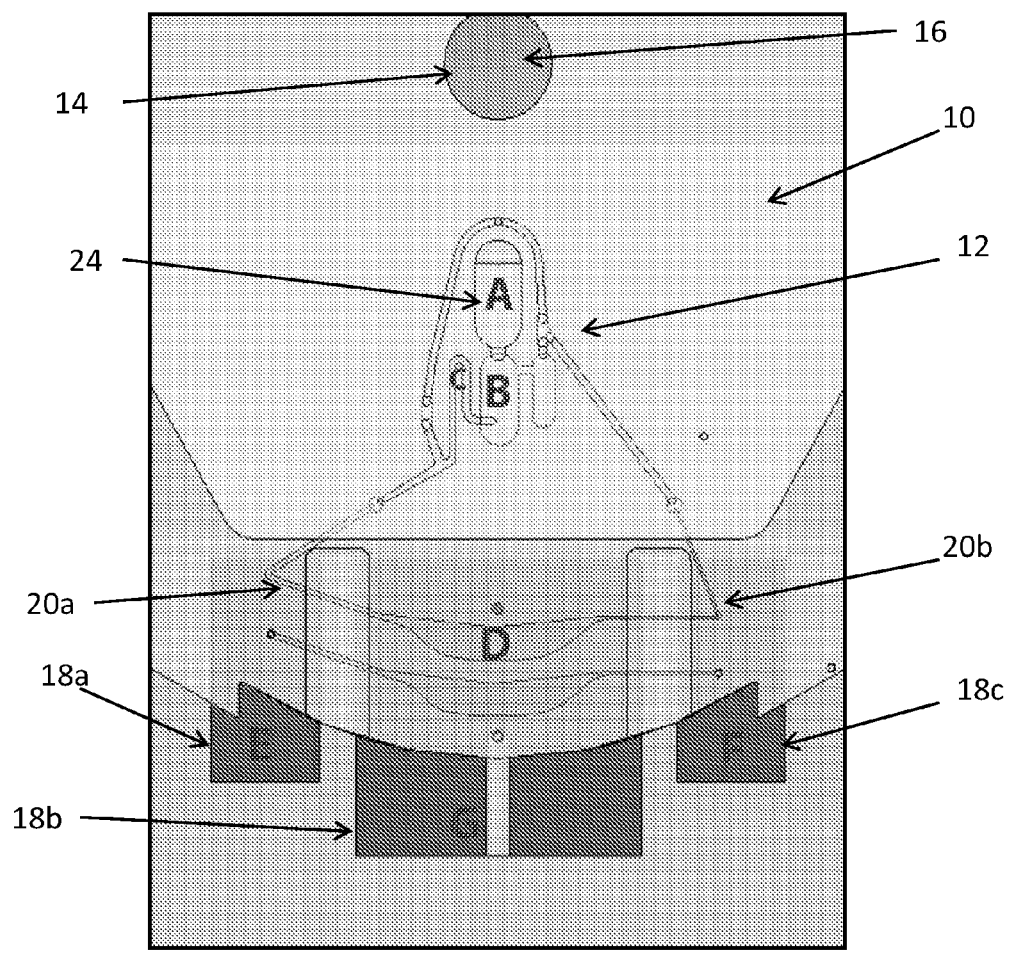
FIG. 1 illustrates a top down view of a portion of a microfluidic CD having a microfluidic feature capable of conducting both lysis and PCR on a CD.

FIG. 1 illustrates a top down view of a portion of a microfluidic compact disc (CD) 10 having a microfluidic feature 12 capable of conducting both lysis and PCR on a CD. The microfluidic CD 10 is typically a multi-layer structure made of one or more PDMS layers sandwiched between polycarbonate (PC) discs using a pressure-sensitive adhesive (PSA). U.S. Patent Application Publication No. 2008-0110500, which is incorporated by reference herein, describes additional details regarding the constructions and methods of manufacturing microfluidic features 12 in the microfluidic CD 10. The microfluidic CD 10 has a center of rotation and includes an aperture 14 for receiving a shaft 16 of a motor or the like that is used to impart rotational motion to the microfluidic CD 10.

Figure 3:
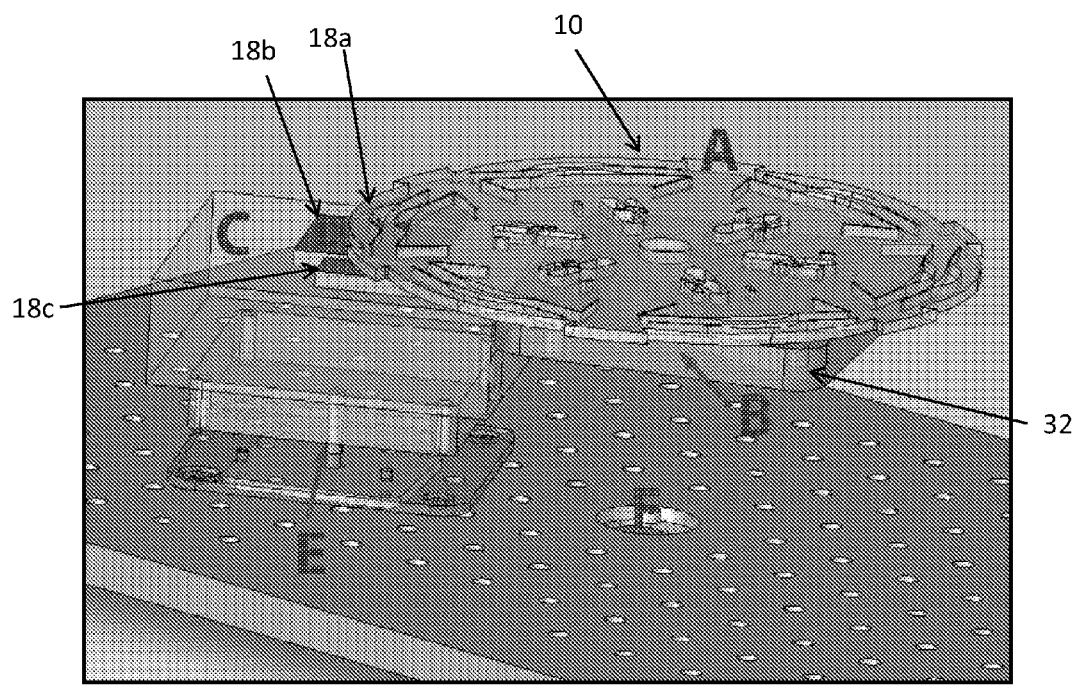
FIG. 3 illustrates a perspective view of system or platform that is used in connection with the microfluidic CD.

The microfluidic CD 10 is shown above a plurality of Peltier thermoelectric devices (TE) labeled as 18a, 18b, and 18c. These TE devices 14a, 14b, and 14c may be mounted on a heat sink C as illustrated in FIG. 3 which can move up and down using an actuation shaft E (as seen in FIG. 3) to bring the TE devices 18a, 18b, 18c in close proximity to the underside of the microfluidic CD 10 to selectively cool/heat portions of the microfluidic features. As explained herein, the outermost TE devices 18a, 18c may be used to cool or freeze fluid contained within the device to form ice-plug valves so that processed sample is retained within the PCR channel or chamber.

The innermost TE device 18b may be used for thermocycling (e.g., heating cycles) for performing the PCR amplification. Referring back to FIG. 1, the microfluidic CD 10 includes a lysis chamber identified as chamber A in FIG. 1. The lysis chamber may be filed with beads or the like that move in response to movement of the magnetically responsive element and disrupt the sample. The beads may be made from glass or zirconium/silica or other materials. For instance the beads may be in the form of a slurry such as 100 μm diameter zirconia beads (BioSpec Products, Inc., OK, USA) in a 1% (w/w) solution of polyvinylpyrrolidone (PVP) (BASF, Ludwigshafen, Germany-Luviskol K90). In still other embodiments, such as that illustrated in FIG. 4, the lysis chamber contains a magnetically responsive element that moves or oscillates back-and-forth in response to interaction with stationary off-board magnets that are disposed underneath the CD (identified by arrow B) as illustrated in FIG. 3. U.S. Patent Application Publication No. 2007-0125942, which is incorporated by reference as if set forth herein, discloses additional details of devices and methods of disrupting biological samples using magnetic elements disposed in a CD-like structure.

Referring back to FIG. 1, the lysis chamber A is coupled to a clarification chamber identified as chamber B. The clarification chamber B is coupled to a siphon valve identified as element "C" in FIG. 1. The siphon valve is used to fill the PCR channel or chamber illustrated as element "D" in FIG. 1. Various reagents may be provided in the chambers/channels as lyophilized reagents. As seen in FIG. 1, the outermost TE devices 18a, 18c may be used to cool or freeze fluid contained within the device to form ice-plug valves so that microchannels 20a, 20b can become selectively plugged or unplugged in response to selective cooling and heating by TE devices 18a, 18c.

Figure 2:
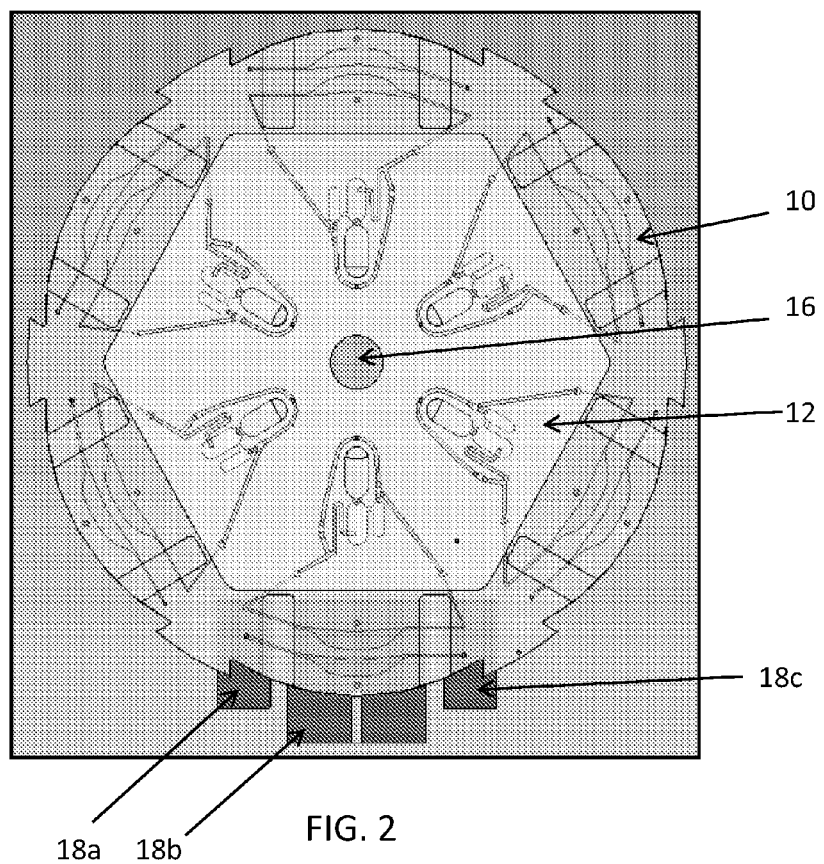
FIG. 2 illustrates a top down view of the microfluidic CD mounted for rotation about a central axis. The CD includes six separate test regions.

FIG. 2 illustrates a top down view of the microfluidic CD 10 mounted on a shaft 16 for rotation about a central axis. The shaft 16 is a spindle or the like that is coupled to a motor may be used to rotate the microfluidic CD much in the same way that CD or DVD discs are turned in standard audio/visual equipment. FIG. 2 illustrates six (6) separate lysis/PCR features formed on a single microfluidic CD 10. Thus, multiple samples can be processed in a single run. Also, while FIG. 2 illustrates only one set of TE devices 18a, 18b, 18c adjacent to one lysis/PCR station, it should be understood that additional TE devices may be positioned about the periphery of the microfluidic CD such that the other lysis/PCR features can be heated/cooled simultaneously.

FIG. 3 illustrates a perspective view of system or platform that is used in connection with the microfluidic CD 10. As seen in FIG. 3, the microfluidic CD 10 also identified as "A," is positioned above a plurality of stationary magnets (identified as B in FIG. 3). The stationary magnets B may be mounted in a frame or holder or the like so that they may be positioned underneath the microfluidic CD 10 (see also FIG. 6). The stationary magnets B interact with the magnetically responsive element located in the lysis chamber (see, e.g., FIGS. 4, 5A, and 5B and associated description) to cause movement of the glass beads to disrupt the sample. In FIG. 3, the support shaft 16 for the microfluidic CD is omitted for clarity. The support shaft 16 is coupled to a motor (element F in FIG. 3) that is used to rotate the microfluidic CD 10. Element "C" in FIG. 3 refers to the heat sink that is coupled to the TE devices 18a, 18b, 18c. An actuation shaft (element E in FIG. 3) is coupled to the heat sink C for moving the same up and down. The TE devices 18a, 18b, 18c can thus be selectively brought into close proximity to the microfluidic CD 10 to plug channels. The system may optionally include optics for fluorescent illumination and detection. For example, an LED may be mounted above the respective channels (e.g., PCR channel) to excite the sample. A photo multiplier tube (PMT) or the like mounted at an angle may be used to detect fluorescent light.

The system includes a power source (not shown) that is able to power the motor F for rotating the microfluidic CD 10 as well as powering the TE devices 18a, 18b, 18c. The power source may also power other hardware such as the illumination and detection systems. The system includes a control system that may be implemented as a computer or microprocessor (or multiple microprocessors) that control the timing and control of the microfluidic CD spinning, thermocycling, and fluorescent detection. The system can have all of this hardware multiplexed around the periphery of the microfluidic CD such that each device can run simultaneously.

The microfluidic CD 10 itself consists of micro and macro channels, made mostly out of plastic or another suitable material. The material may need to be treated to ensure it is hydrophilic. The hydrophilic surfaces facilitate microfluidic function of the device. All dimensions are on the scale from hundreds of um to mm. The NA amplification channel bottom can be made of metal to facilitate heat performance when in contact with the TEs 18a, 18b, 18c. The entire bottom of the microfluidic CD 10 may be black to enhance fluorescence measurements. Preferably, there should be an optically clear window above the PCR channel to allow optical interrogation. There may be two (2) PCR channels present, such that a simultaneous control reaction can be run for quality control and/or quantification, as pictured in FIGS. 1-3. For example, the second PCR channel may provide fluorescent reference detection.

Most commonly, the microfluidic CDs 10 consist of multi-layer structures made of inexpensive polycarbonate plastic and pressure-sensitive adhesives (PSA). Using relatively simple CNC machines, channel widths of down to 1 mm are machined into stock polycarbonate CDs or plastic sheets. A computer-controlled cutter-plotter is used to cut channel widths as narrow as 200 µm in 100 µm-thick PSA or oil films. Once the appropriate pieces have been designed and machined, they are aligned centrally and radially, and then laminated together using PSA layers.

As an example, the microfluidic CD may consist of no less than 7 layers including: 1) top polycarbonate CD with CNC-machined sample loading, sample removal, and air venting holes (sealed using a thin adhesive film during operation), 2) pressure-sensitive adhesive with channel features cut using a plotter, 3) middle polycarbonate CD with CNC chamber features, 4&5) pressure-sensitive adhesive layers with PCR chamber features cut using a plotter, doubled-up to obtain a higher thickness, 6) solid bottom polycarbonate CD, and 7) thin adhesive foil films cut using a plotter to seal off PCR chambers. Microfluidic CD platforms can involve more layers to accommodate more complex fluidics.

Moreover, different devices and substances can be placed inside the CD during fabrication, such as beads, lyophilized reagents, or filters. The CDs can also be exposed to $O_2$ plasma treatment or functionalized with bovine serum albumin (BSA) to create hydrophilic and hydrophobic surfaces, respectively. The fabrication process usually ends with running the microfluidic CDs 10 through an industrial press to ensure excellent adhesion and sealing between all CD layers.

The following sequence of operations describe on illustrative method of using the microfluidic CD 10 to perform PCR as an example of NA amplification. Any method requiring heat and/or thermocycling could be used. In addition, reverse-transcriptase steps could be incorporated before amplification.

Figure 4:
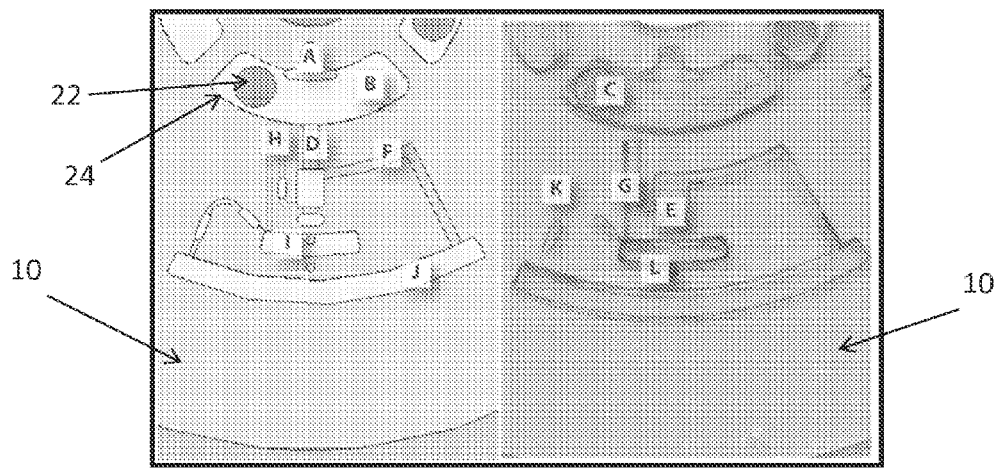
FIG. 4 is a schematic representation of a single lysis device on the CD (left side) along with an image of the same (right side).

The system would work using the operations described below. The order of the various processes are consecutively performed although in other embodiments one or more operations may be omitted or performed in a different order. First, a user obtains a disposable, plastic microfluidic CD 10 that contains the appropriate reagents (likely lyophilized on the microfluidic CD 10) for the particular bacteria(s) and/or virus(es) they wish to detect. The user then takes the sample (previously collected and processed appropriately) and inserts the same into the lysis chamber (chamber A in FIG. 1 or chamber B in FIG. 4). The sample may consist of a direct respiratory sample, processed blood samples, or other biological samples. The user may seal the lysis chamber if the sealing process is not automatic, and places the microfluidic CD 10 in the system. In particular, the microfluidic CD 10 is mounted on the shaft 16 that is coupled to a motor F. Next, the user starts the operation of the platform. The microfluidic CD 10 begins to spin at a relatively low speed. During this time, magnets located inside the microfluidic CD 10 (e.g., inside lysis chamber) interact with stationary magnets off the CD (FIG. 3, element B), causing the magnets inside the microfluidic CD 10 to oscillate in a back-and-forth motion. FIG. 4 illustrates a magnet 22 (or blade C) located within a lysis chamber B of a microfluidic CD 10. An exemplary magnet may include a ferromagnetic disk (model VP721F) available from V&P Scientific, Calif.

The oscillation of the on-CD magnet(s) 22 in the presence of the biological sample and glass beads residing in the lysis chamber causes sample disruption. The NA of interest is released from the bacteria and/or viruses. The speed of the rotation of the microfluidic CD 10 is increased using the motor, causing the sample to leave the lysis chamber and enter the clarification chamber (chamber B in FIG. 1). Here, the CD is spun at such a high speed that debris/inhibitors are spun out of solution and pelleted at the bottom of the clarification chamber, yet the NA of interest stays in solution.

Next, the microfluidic CD 10 is then slowed down via control of the motor, causing the siphon (identified as C in FIG. 1) to prime, and begin filling the PCR channel (element D in FIG. 1). The microfluidic CD is then spun at a slightly higher rate to finish the PCR channel filling. The microfluidic CD 10 is then stopped, and aligned with Peltier thermoelectric (TE) devices 18a, 18b, 18c (illustrated in FIGS. 1-3) mounted on a heat sink (element C in FIG. 3). The TEs 18a, 18b, 18c are then actuated into contact or near contact with the microfluidic CD 10 from beneath. Element E in FIG. 3 shows an actuation shaft.

Power is applied to the outer two TEs 18a, 18c in a cooling mode, such that the liquid at the end of the PCR channel freezes so as to create an ice-plug valve. For example, with reference to FIG. 2, the ice-plugs may form in microchannels 20a, 20b. Next, the middle TE 18b (or multiple middle TEs) are powered on, and performs the required thermocycling/heating for NA amplification. In the case of real-time fluorescence monitoring of NA amplification (e.g., real-time PCR or qPCR), fluorescence readings can be taken during amplification. For example, an LED mounted above the PCR (or other) channel can excite the sample in the channel, and a PMT mounted at an angle to the channel can be used to detect the emission. Different LEDs and optical filters may be included to monitor for more than one fluorophore (and hence more than one analyte). Fluorescence is monitored during amplification to detect the NA analyte(s) of interest. After ~1 hour, the process is finished and the user returns to the system to obtain the results, likely relayed through the use of a computer screen or other output.

FIGS. 4-12 illustrate an alternative microfluidic system that includes the benefits of (1) sample pre-metering; (2) hydraulic capillary valve which leads to higher rotation speeds (i.e., burst frequency) to be achieved compared to normal, single-force capillary valves; (3) in-line capillary valve with the siphon to prevent re-priming of microfluidic features; and (4) self venting.

FIG. 4 (left side) is a schematic representation of a single lysis device feature on the microfluidic CD 10 (presented in duplicate for clarity) along with an image of the same (right side). The following labeled features A-L are as follows: A—sample inlet port, B—lysis chamber, C—magnetic lysis blade, D—hydraulic capillary valve, E—clarification (upper) and capture (lower) chambers, F—metering channel, G—siphon capillary valve, H—siphon, I—collection chamber, J—waste chamber, K—self-venting channels, L—sample collection port.

Figures 5A, 5B:
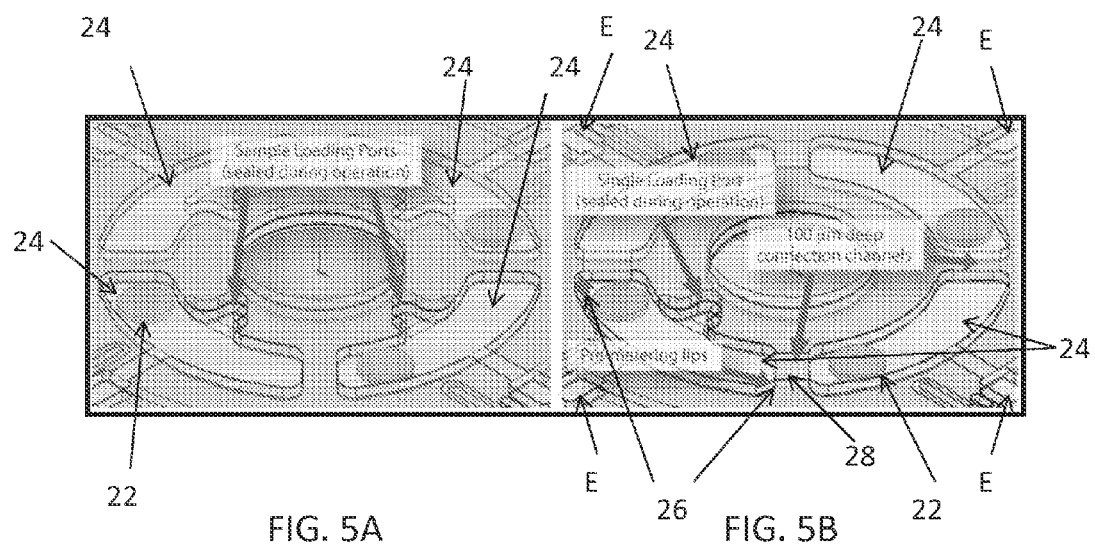
FIG. 5A illustrates one embodiment of a microfluidic CD that includes four (4) separate lysis chambers each with its own sample loading port. Magnetically responsive elements can be seen in each of the four lysis chambers.
FIG. 5B illustrates another embodiment of a microfluidic CD that includes four (4) separate lysis chambers that are connected for processing of a single sample with a single sample loading port.

FIG. 5A illustrates one embodiment of a microfluidic CD 10 that includes four (4) separate lysis chambers 24 each with its own sample inlet port. FIG. 5B illustrates another embodiment of a microfluidic CD that includes four (4) separate lysis chambers that are connected for processing of a single sample. The connected version in FIG. 5B allows distribution and pre-metering of the sample while keeping the beads (not shown) and magnets 22 isolated. A vertical lip 26 is used to prevent beads from transferring into adjacent lysis chambers 24. The connection channel 28 is dimensioned to prevent transfer of both the beads and the magnets 22 and is about 100 μm deep. While four (4) lysis chambers 24 are illustrated, more or less may be used in a single microfluidic CD 10.

The device of FIG. 5A provides multiplexed processing of four (4) independent samples each through a single device, while the device of FIG. 5B provides multiplexing of a single sample distributed to four (4) separate devices. In the non-connected embodiment of FIG. 5A, four (4) distinct lysis chambers 24 are provided, each with its own sample loading inlet allowing the introduction of 50-75 uL of sample. In the connected embodiment of FIG. 5B, there is only one (1) sample inlet port provided, yet four (4) distinct lysis chambers 24 remain. The lysis chambers 24 are connected through a radial channel 28 in an upper CD layer, which is only 100 μm thick. This allows liquid communication between the four (4) lysis chambers 24, yet prevents the magnets 22 and lysis beads (slightly >100 μm in diameter) from traveling between the four (4) chambers and re-distributing themselves. The end result is a single sample, with a volume ranging from 200-300 μL, that is distributed and processed into four (4) distinct volumes, such that each of the four (4) sub-samples can be subjected to, for example, four (4) different amplification and detection assays after lysis processing.

The liquid sample distribution in the embodiment of FIG. 5B occurs via two processes. The first is centrifugal force applied during lysis. Rotation at ~650 RPM forces the liquid towards the bottom of the chamber, and allows excess to spill through the 100 μm connection channel into adjacent lysis chambers 24. Note also the presence of the small lip 26 (i.e., vertical lip) in the lysis chamber 24 beneath the connection channel 28; this ensures that, as the sample is distributed, each lysis chamber 24 captures and retains the minimal volume necessary for processing. The second distribution method is through the motion of the magnets 22 and beads. This helps distribute the sample radially around the microfluidic CD 10, and overcome any capillary valve effects present at the exits of the connection channels. The sample distribution and lysis functions occur simultaneously.

FIG. 6 is a schematic showing the microfluidic CD system along with the underlying stationary permanent magnets 30. The permanent magnets 30 may include nickel plated, neodymium-iron-boron magnets. A motor coupled to spindle passing (not shown) through the center hold and rotate of the microfluidic CD 10 about its central axis. There are four (4) permanent stationary magnets 30 shown mounted in a holder 32 that is situated beneath the microfluidic CD 10. There are four (4) lysis chambers 24 in the microfluidic CD 10, each with its own magnetic lysis blade 22 that, as explained below, moves back and forth in the lysis chamber 24. During operation, the microfluidic CD 10 is rotated about its axis. FIGS. 7A, 7B, and 7C illustrate a sequence of photographs illustrating the snap-drag motion as the on-CD magnetic lysis blades 22 interact with the stationary off-CD magnets 30 (not shown). As seen in the sequence, the magnetic lysis blade 22 moves from a stationary position at one side of the lysis chamber 24 to the opposing side of the lysis chamber 24 in a snapping motion and is subsequently dragged along a wall of the lysis chamber 24 back to the starting position as the microfluidic CD 10 is rotated.

Figure 8:
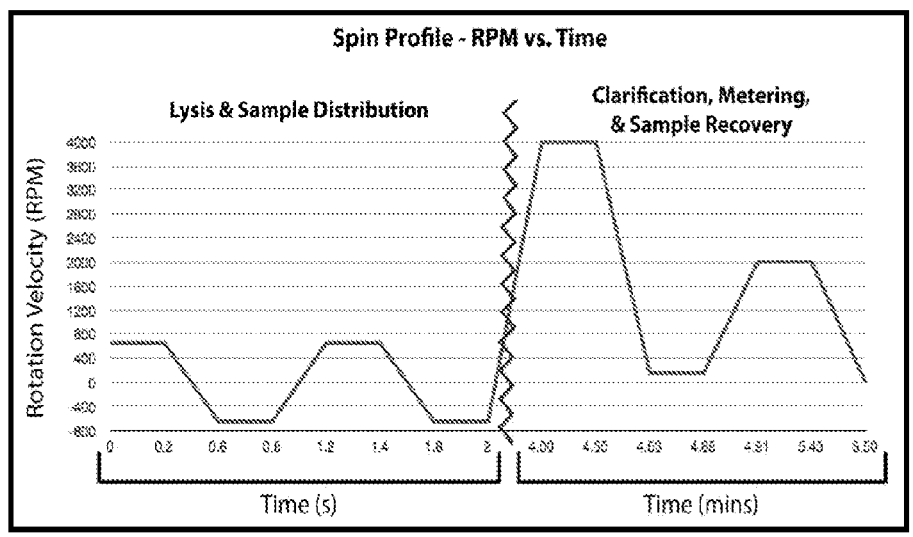
FIG. 8 illustrates the typical spin profile (RPM v. time) for the CD system.

FIG. 8 illustrates the typical spin profile for the CD system. Lysis and sample distribution involves oscillation of the microfluidic CD 10 in a clockwise, counter-clockwise motion at +/−650 RPM. This is repeated for a total of four (4) minutes. The next step involves clarification (4000 RPM), followed by siphon priming (150 RPM), and sample recovery (2000 RPM).

Figure 9:
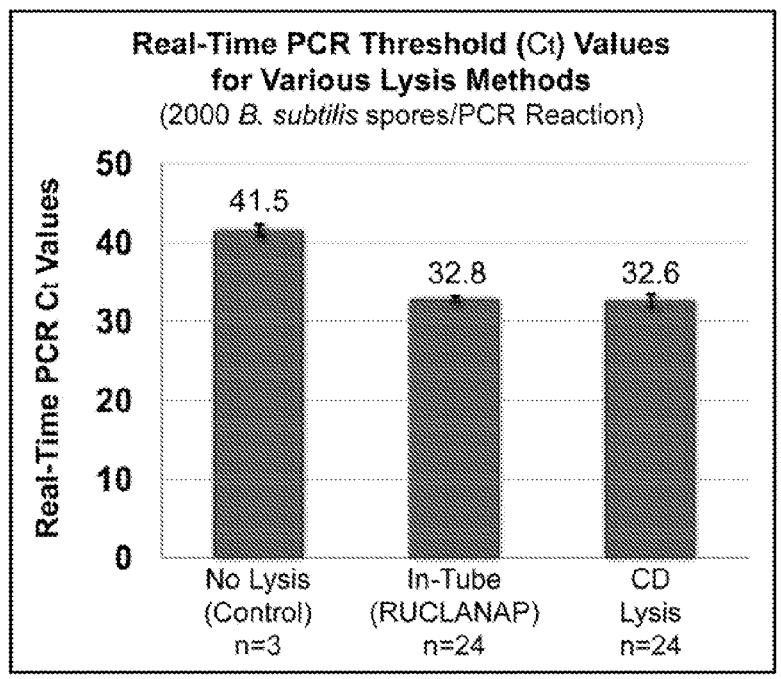
FIG. 9 illustrates the lysis efficiency of a standard in-tube, bead-beating lysis kit as compared to the CD system (control also included).

FIG. 9 illustrates the lysis efficiency of a standard in-tube, bead-beating lysis kit as compared to the CD system. Real-time PCR was performed directly on *Bacillus subtilis* spore samples, and the $C_t$ value plotted. Data shown is averaged. The microfluidic CD-based lysis process shows equivalent lysis efficiency.

Exemplary Method of Use

A sample containing cells or other structures that contain therein nucleic acid (NA) or other analytes/target for testing may be used with the device. Respiratory virus samples are used as an example nucleic acid sample here. It should be understood, however, that any sample requiring lysis and clarification could be used in the system.

The CD system would work as follows. First, the user obtains a disposable, plastic microfluidic CD 10 that contains the appropriate lysis beads and magnets 22 in the lysis chamber 24. Next, the user takes the sample (previously collected and processed appropriately) and inserts it into the lysis chambers 24 (FIG. 4—element B) through the sample inlet port (FIG. 4—element A). The user may insert a single sample to the connected microfluidic CD 10 for processing of a single sample (e.g., FIG. 5B), or four (4) separate samples into the disconnected microfluidic CD 10 (FIG. 5A). The user then seals the lysis chamber(s) if not automatically sealed, and places the microfluidic CD 10 in the drive system. FIG. 6 shows the microfluidic CD 10 and the permanent magnet platform 32 where the microfluidic CD 10 is mounted.

Next, the user starts the operation of the platform. The microfluidic CD 10 begins to spin at a relatively low speed. During this time, magnetic blades 22 inside the microfluidic CD 10 (FIG. 4—element C) interact with stationary magnets 30 off the microfluidic CD 10 (FIG. 6), causing the magnetic blades 22 inside the lysis chamber 24 to oscillate. FIGS. 7A-7C illustrate the oscillatory motion of the magnetic blades 22. The oscillation of the on-CD magnetic blades 22 in the presence of the biological sample and lysis beads residing in the lysis chamber(s) 24 causes sample disruption. The nucleic acid of interest is released from the bacteria and/or viruses.

Next, the rotational speed of the microfluidic CD 10 is increased, causing the sample to burst the hydraulic capillary valve (FIG. 4—element D), leave the lysis chamber 24, and enter the clarification chamber (FIG. 4—element E). Here, the microfluidic CD 10 is spun at a high speed such that debris/inhibitors are spun out of solution and pelleted at the bottom of the clarification chamber in the capture chamber, yet the nucleic acid of interest stays in solution. Additionally during this step, volume definition occurs, with excess sample moving out through the metering channel (FIG. 4—element F) and into the waste (FIG. 4—element J). This leaves a total of 25 μL of sample combined in the clarification and capture chambers, siphon capillary valve (FIG. 4—element G), and partially in the siphon (FIG. 4—element H).

A hydraulic capillary valve is used in the microfluidic CD device 10. This is a valve that relies both on capillary valve forces and hydraulic forces to retain the fluid inside the lysis chamber 24 during processing (FIG. 4—element D). Once the sample inlet port(s) A is sealed after loading, there is no connection to the atmospheric environment behind the liquid. This means that, in addition to the normal capillary forces present on the capillary valve at the exit of the lysis port (FIG. 4—element D), there is a low-pressure environment behind that liquid, further preventing the sample from moving on and into the clarification chamber (FIG. 4—element E) during lysis. This double-force, hydraulic capillary valve allows higher rotation speeds (viz., burst frequency) to be achieved as compared to a normal, single-force capillary valve. This translates to the ability to perform more efficient lysis at higher speeds without worry of the sample bursting into the clarification chamber prematurely. The downside of the capillary hydraulic valve is that a much higher rotation speed must be achieved in order to reach the burst frequency and move the liquid into the clarification chamber. In this system, however, the centrifugal forces required for clarification (4000 RPM) far exceed the burst frequency of the hydraulic capillary valve (~1000 RPM), thus adding no additional requirements to the hardware system.

After clarification, the rotational speed of the microfluidic CD 10 is reduced to 150 RPM, allowing capillary forces in the hydrophilic siphon to overcome the centrifugal forces, thus priming the siphon valve G (with reference to FIG. 4). Capillary forces draw the liquid through the entire length of the siphon H and to a point diametrically "lower" than the clarification chamber E, at the entrance of the sample collection chamber I. The microfluidic CD 10 is then slowly sped up to 2000 RPM, resulting in siphon action pumping only the supernatant from the clarification chamber E and siphon capillary valve G into the sample collection chamber I. Approximately 20 μL of sample is deposited into the sample collection chamber I, and the "dirty" sample remains in the capture chamber. After <10 minutes, the process is finished and the user returns to the system to obtain the processed nucleic acid samples. A typical spin profile is shown in FIG. 8.

The microfluidic CD 10 itself consists of micro and macro channels, made mostly out of plastic or another suitable material as described above (e.g., PDMS). The microfluidic CD 10 can be made of multiple layers which are then bonded together. The material may need to be treated to ensure it is hydrophilic. The hydrophilic surfaces facilitate microfluidic function of the device. All dimensions are on the scale from hundreds of μm to mm. The bottom of the microfluidic CD 10 needs to remain thin enough to facilitate magnetic action, but thick enough to prevent the magnetic force from damaging the microfluidic CD 10. There may be several devices (two or more) present on each microfluidic CD 10. Any suitable permanent magnet, magnetic lysis blade, and lysis bead mixture may be used in the system. The hardware system supporting the CD would consist of a motor for spinning, a stationary magnet holder (FIG. 6), a power source, and a control system (computer). The control system would provide the appropriate timing and control for CD spinning.

Description of the Biological Testing

*Bacillus subtilis* spores (difficult to lyse) were used as samples. Spores samples were placed in the microfluidic CD 10, and a gold-standard control was run which consisted of a top-performing, off-the-shelf bead-beating lysis kit. The samples were lysed, and a *B. subtilis* gene was amplified using real-time PCR. The $C_t$ value (at which amplification is detectable via fluorescence) was measured. A lower $C_t$ value indicates more efficient amplification via a more efficient lysis. Several experiments were run in replicates using several different microfluidic CDs 10. The results show equivalent $C_t$ values for both the gold-standard, in-tube method and the microfluidic CD method, confirming efficient lysis on the CD (FIG. 9). The $C_t$ values for both methods (each n=24) are statistically identical, thus validating equivalent lysis performance for the microfluidic CD-based method. The no-lysis control group had a higher $C_t$ to be expected from residual DNA adsorbed on the spores upon sporulation.

An embodiment of the above-described microfluidic CD 10 now follows that performs nucleic acid amplification via PCR followed by nucleic acid detection via a microarray. Thus, this contrasts with some prior embodiments in which detection is performed via real-time PCR. Thus, this system tackles the additional complications involved in preparing a PCR product for DNA microarray hybridization, and performing DNA microarray hybridization. This particular embodiment allows for detection of a large panel of analytes (>>4-6 analytes) as compared to the use of real-time PCR which limits the number of analytes that can be simultaneously detected.

The first step involves a mechanical bead-beating lysis step as explained herein which uses moving magnetic blades 22. Included here is and removal/destruction of PCR inhibitors by the combined use of specific capture resins and/or heat. After sample preparation and volume definition, the sample is subjected to a heated/thermocycled NA amplification step (PCR), which may also include a reverse-transcriptase step (RT-PCR), especially in the case of RNA-based viral diagnostics. The use of TE devices 18a, 18b, 18c may be employed for thermocycled NA amplification as explained herein. After this, the PCR products are prepared for DNA microarray hybridization. Hybridization is then performed by flowing the hybridization mixture across a DNA microarray 34; this is followed by flowing a wash solution across the DNA microarray 34, and then reading the microarray 34 for detection/diagnosis.

The microfluidic CD 10 may accept a sample from a single patient, such that a large number of analytes can be diagnosed from a single patient (e.g., FIG. 5A). Also, the microfluidic CD 10 may accept four (4) separate samples from four (4) separate patients, to scan for a smaller number of analytes from a larger number of patients (e.g., FIG. 5A). The microfluidic device can be made of plastic (for example injection molding) and then utilized in a clinical setting to perform rapid (<1 hour) analysis for agents of interest (viz., respiratory viruses). The device may also be used in a research setting.

Figures 10A, 10B:
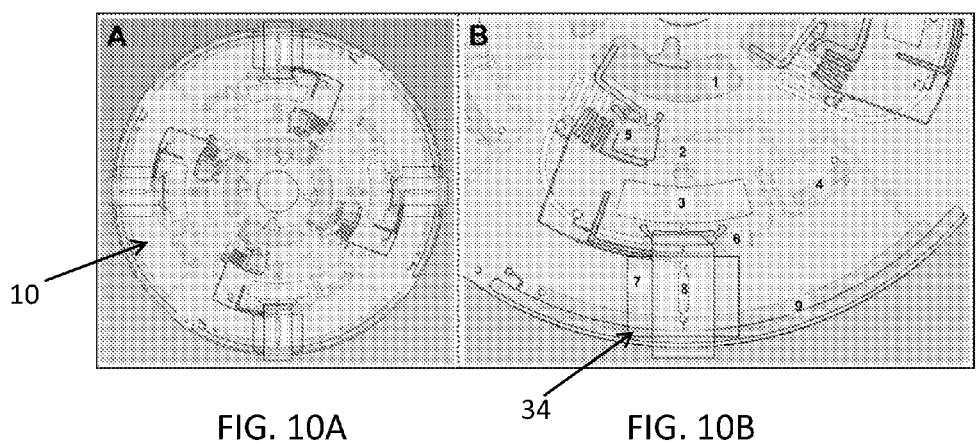
FIG. 10A illustrates a top-down view of a microfluidic sample-to-answer respiratory virus detection CD.
FIG. 10B shows a close-up image of a single device on the CD of FIG. 10A. Illustrated include the lysis and homogenization chamber (1), the clarification and volume definition chamber (2), the PCR microchamber (3), the exonuclease digestion chamber (4), the wash buffer reservoir in a layer above the hybridization buffer reservoir (5), mixing chambers (6), part with imbedded DNA hybridization chamber (7), microarray slide with printed DNA microarray (placed face down into DNA microarray chamber) (8), and waste chambers (9).

This CD-based sample-to-answer system can be designed, for example, to detect sixteen (16) respiratory viruses from a single patient. The system functions by first directly accepting a respiratory sample (nasopharyngeal aspirate or swap, ~200-400 μL volume in eluted PCR buffer) from a single patient, splitting this sample into four (4) separate aliquots, and then performing lysis and homogenization on each separated sample (FIGS. 10A and 10B). After stopping the microfluidic CD 10 and bringing it into contact with heat (using TE devices 18a, 18b, 19c) to perform a heating step to eliminate PCR inhibitors (95° C. for ~2 minutes, performed using heaters in combination with ice-valves), the prepared sample is clarified, the volume defined (FIG. 10B—element 2), and the liquid samples sent to four (4) respective PCR chambers, wherein four (4) separate multiplexed RT-PCR reactions occur (FIG. 10—element 3); each PCR chamber contains the appropriate dried and/or lyophilized reagents, including additional PCR buffer components (viz., $MgCl_2$), specific primers, and polymerases that reconstitute upon contact with the prepared sample in PCR buffer. Each PCR assay amplifies the target material for detection of four (4) clinically relevant respiratory viruses. Thus, the entire CD detects sixteen (16) different viruses from a single patient's sample.

After four (4) simultaneous PCR reactions, the samples are then spun into exonuclease chambers, where lyophilized exonuclease enzymes reconstitute, and the double-stranded amplicons are digested into single strands in preparation for detection via DNA microarray hybridization (FIG. 10B—element 4); this requires heating at 37° C. while spinning. After exonuclease digestion, the samples are spun into a mixing chamber for mixing with liquid hybridization buffer (FIG. 10B—element 6); this hybridization buffer was previously loaded by the user, and held back by a serial siphon valve. After oscillation of the microfluidic CD 10 to perform mixing, the four (4) separate hybridization solutions (mixed hybridization buffer and single-stranded PCR products), are centrifugally pumped into a hybridization layer of the microfluidic CD 10, and flowed across their respective DNA microarrays 34 (FIG. 10B—element 7) printed on plastic slides (FIG. 10B—element 8) and previously mounted onto the microfluidic CD 10. This step requires heating at 42° C., for increased hybridization specificity, and is performed while spinning.

Next, a wash buffer (previously loaded by the user into the hybridization layer and also held back by a serial siphon valve) is flowed across the DNA microarrays 34 to remove non-specifically adsorbed DNA. Finally, the DNA microarrays 34 are spun dry, and the fluorescence read. The fluorescence intensity data from the microarray scans are used to validate successful completion of the assay, and make a diagnosis as to which, if any, of the sixteen (16) viruses have infected the patient. The entire system is able to complete this analysis within one hour.

The microfluidic CD 10 has been carefully designed to ensure optimal modularity and ease of fabrication. The components of the microfluidic CD subjected to the most intense thermal conditions (viz., PCR) have been placed within the bottom CD layers, where thermal bonding can occur before bonding with other CD materials not compatible with thermal bonding processes. The use of a thin film for the CD-bottom ensures good thermal coupling between the CD chambers and thermal components. Note the CD channels need to be hydrophilic to facilitate siphon valve priming. For example, if plastic is used as the microfluidic CD 10 material, hydrophilization could be performed by oxygen-plasma treatment.

Modular insertion of the DNA microarray 34 into the top of the disc allows the manufacturer responsible for DNA microarray printing to themselves insert the DNA microarray 34 into the microfluidic CD 10. This further allows for modularity in the assay that can be run, as different DNA microarrays 34 can be utilized as needed. Finally, the microfluidics have been designed in consideration of the hardware requirements. All thermocycling and ice-valving procedures occur in the lower layers of the microfluidic CD 10. This provides spatial freedom below to disc for mounting of thermal hardware. Placement of the DNA microarray 34 on the top of the microfluidic CD 10 ensures the thermal and optical hardware will not interfere. Moreover, the fluorescence detection system needs only needs to go through a single interface (the plastic microarray slide), which simplifies the focusing and sensitivity requirements of that system.

Figures 11A, 11B, 11C, 11D, 11E, 11F, 11G, 11H, 11I, 11J:
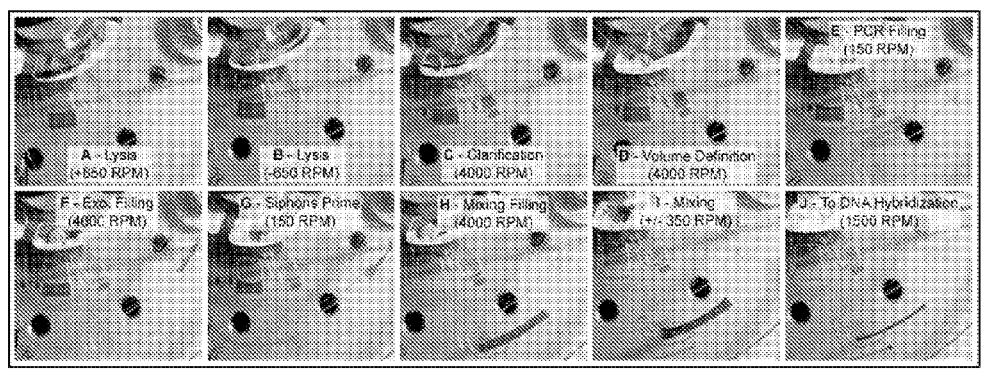
FIGS. 11A-11J show a sequence of strobe photographic images showing functionality of the microfluidic plastic viral detection CD.

All siphons prime on queue, all capillary valves hold back the fluid as desired, and the PCR microchamber filling is complete and uniform, and mixing of the PCR fluid and hybridization buffer is efficient. FIG. 11 shows a time-lapse sequence of the microfluidic plastic CD in operation. The microfluidic function of the lysis and clarification steps are shown in FIGS. 11A-B. After clarification and volume definition (FIGS. 11C-D), the rotational speed of the microfluidic CD 10 is lowered to allow the single siphon to prime and fill the PCR microchamber (FIG. 11E). At this point, the first serial siphon on the hybridization buffer reservoir is primed. The exit of the PCR microchamber into the exonuclease chamber acts as a capillary valve, keeping the PCR liquid from moving on before ice-valving. The volume definition function is adequate, providing enough liquid to uniformly fill the PCR microchamber, but not too much liquid that it prematurely bursts into the exonuclease chamber.

After stopping for PCR, the spin-speed is then increased to pump the PCR liquid into the exonuclease chamber (FIG. 11F). After slowing down again, the exonuclease siphon primes, as does the second serial siphon of the hybridization buffer reservoir (FIG. 11G). The microfluidic CD 10 is then sped up, thus pumping the liquids from the exonuclease chamber and hybridization buffer reservoir into the common mixing chamber (FIG. 11H). Once the rotational speed of the microfluidic CD 10 is decreased again, the mixing chamber siphon primes. The outlet of this siphon channel acts as a capillary valve, with a burst frequency such that mixing can be performed at speeds up to ~400 RPM. The liquids re-mix uniformly by oscillating the microfluidic CD spin direction at +/−350 RPM (FIG. 11I) with a high acceleration (1000 RPM/s), and then the microfluidic CD spin speed is increased (1500 RPM) to pump the fluid into the hybridization chamber in the DNA hybridization fluidics layer (not shown) (FIG. 11J).

Figure 12:
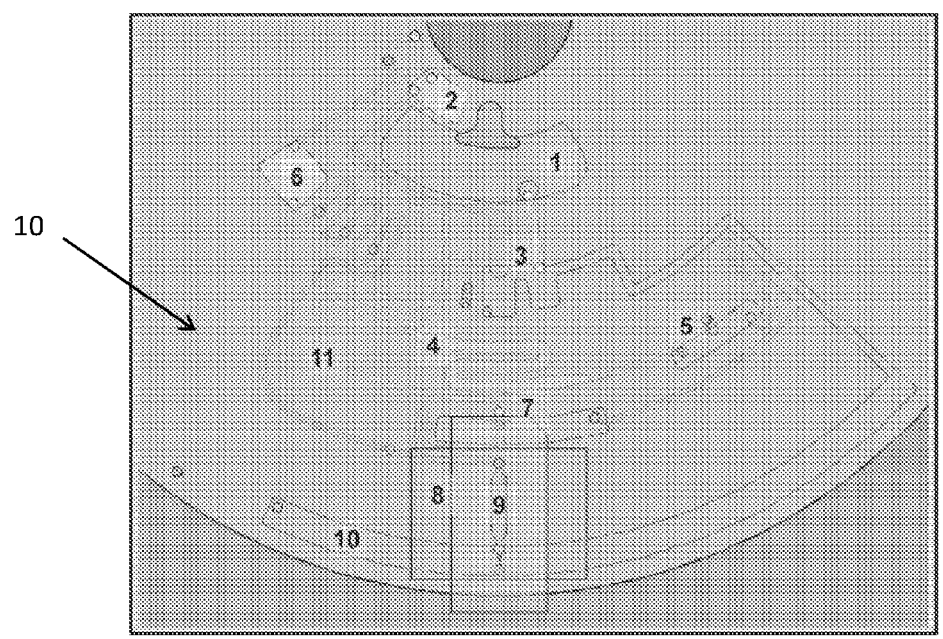
FIG. 12 illustrates an alternate design of the microfluidic sample-to-answer respiratory virus detection CD. A single device or microfluidic feature is illustrated in FIG. 12 including a lysis and homogenization chamber (1), PCR buffer reservoir (2), double metering chamber (3) for volume definition and mixing with PCR buffer, PCR microchamber (4), exonuclease digestion chamber (5), wash buffer reservoir (6), mixing chamber (7), part with imbedded DNA hybridization chamber (8), microarray slide with printed DNA microarray (9) (placed face down into DNA microarray chamber), waste chamber (10), and self-venting channel (11).

The microfluidic CD 10 shown in FIGS. 10A and 10B is only one embodiment of what the microfluidic CD 10 may look like, and how it may function. FIG. 12 shows another embodiment that includes additional features, such as less reliance on dried/lyophilized reagents and a self-venting mechanism. This embodiment also features a way of metering a volume and mixing it with liquid PCR buffer, in preparation for PCR.

A single device or microfluidic feature is illustrated in FIG. 12 including a lysis and homogenization chamber (1), PCR buffer reservoir (2), double metering chamber (3) for volume definition and mixing with PCR buffer, PCR microchamber (4), exonuclease digestion chamber (5), wash buffer reservoir (6), mixing chamber (7), part with imbedded DNA hybridization chamber (8), microarray slide with printed DNA microarray (9) (placed face down into DNA microarray chamber (9)), waste chamber (10), and self-venting channel (11).

While embodiments of the present invention have been shown and described, various modifications may be made without departing from the scope of the present invention. The invention, therefore, should not be limited, except to the following claims, and their equivalents.

What is claimed is:

1. A system for processing a sample comprising:
   a microfluidic CD in the form a rotatable disc, the disc containing a plurality of separate lysis chambers therein, each lysis chamber being connected to an adjacent lysis chamber via a connection channel, one of the lysis chambers further comprising an inlet port configured to load a sample into the lysis chambers;
   a magnetic lysis blade and lysis beads disposed in each of the lysis chambers;
   a plurality of clarification chambers disposed radially outward of the lysis chambers, each clarification chamber connected to an associated lysis chamber via a hydraulic capillary valve;

a plurality of stationary magnets disposed adjacent to and separate from the microfluidic CD, the plurality of stationary magnets configured to magnetically interact with each of the magnetic lysis blades upon rotation of the microfluidic CD; and wherein the connection channel is dimensioned to prohibit transfer of the magnetic lysis blade and lysis beads but does allow for the passage of fluids.

2. The system of claim 1, wherein the connection channels comprise channels formed in the microfluidic CD that are disposed above a bottom surface of the respective lysis chambers.

3. The system of claim 1, wherein the magnetic lysis blade moves from a stationary position at one side of the lysis chamber to the opposing side of the lysis chamber in a snapping motion and is subsequently dragged along a wall of the lysis chamber back to the starting position as the microfluidic CD is rotated.

4. The system of claim 1, wherein the plurality of separate lysis chambers comprises at least four lysis chambers and at least four clarification chambers.

5. The system of claim 1, wherein the inlet port of the lysis chamber is configured to be sealed from the external environment.

6. The system of claim 1, further comprising a siphon capillary valve operatively coupled to each of the plurality of clarification chambers.

7. The system of claim 6, wherein each siphon capillary valve is operatively coupled to a collection chamber.

8. The system of claim 7, wherein each clarification chamber is also operatively coupled to a respective waste chamber and a self-venting channel couples the respective waste chamber to the respective collection chamber.

9. The system of claim 1, further comprising one or more thermoelectric devices configured to heat or cool the microfluidic CD.

10. The system of claim 9, wherein the thermoelectric devices are moveable relative to the microfluidic CD.

11. A system for processing a sample comprising:
a microfluidic CD in the form a rotatable disc, the disc containing a plurality of separate lysis chambers therein, each lysis chamber being connected to an adjacent lysis chamber via a connection channel, one of the lysis chambers further comprising an inlet port configured to load a sample into the lysis chambers;
a magnetic lysis blade and lysis beads disposed in each lysis chamber, wherein the connection channel is dimensioned to prohibit transfer of the magnetic lysis blade and lysis beads but does allow for the passage of fluids;
a plurality of stationary magnets disposed adjacent to and separate from the microfluidic CD, the plurality of stationary magnets configured to magnetically interact with each of the magnetic lysis blades upon rotation of the microfluidic CD;
a thermoelectric device configured to heat or cool the microfluidic CD, the thermoelectric device being moveable relative to the microfluidic CD;
a plurality of PCR chambers disposed in the microfluidic CD and radially outward of the lysis chambers, each PCR chamber operatively coupled to one of the lysis chambers, the PCR chamber containing therein PCR reagents;
a plurality of exonuclease chambers disposed in the microfluidic CD, each exonuclease chamber configured to receive nucleic acid from a respective PCR chamber, the exonuclease chambers containing therein exonuclease; and
at least one nucleic acid microarray configured to receive nucleic acid from at least one of the plurality of exonuclease chambers.

12. The system of claim 11, wherein each exonuclease chamber is associated with its own nucleic acid microarray.

13. The system of claim 11, wherein the nucleic acid microarray is modular and configured to be removably secured to the microfluidic CD.

* * * * *